(12) United States Patent
Harbers et al.

(10) Patent No.: US 9,945,787 B2
(45) Date of Patent: Apr. 17, 2018

(54) INCREASING THE USABLE DYNAMIC RANGE IN PHOTOMETRY

(71) Applicant: Roche Diagnostics Operations, Inc., Indianapolis, IN (US)

(72) Inventors: Rik Harbers, Cham (CH); Kurt Schildknecht, Huenenberg (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 568 days.

(21) Appl. No.: 13/737,523

(22) Filed: Jan. 9, 2013

(65) Prior Publication Data
US 2013/0130400 A1 May 23, 2013

Related U.S. Application Data

(63) Continuation of application No. PCT/EP2011/061677, filed on Jul. 8, 2011.

(30) Foreign Application Priority Data

Jul. 21, 2010 (EP) .................................... 10170345

(51) Int. Cl.
*G01N 21/00* (2006.01)
*G01N 21/75* (2006.01)
(Continued)

(52) U.S. Cl.
CPC ................ *G01N 21/75* (2013.01); *G01J 3/28* (2013.01); *G01J 3/42* (2013.01); *G01N 21/255* (2013.01)

(58) Field of Classification Search
CPC ............. Y10T 436/25; Y10T 436/2575; Y10T 436/115831; Y10T 436/12; A61B 8/56;
(Continued)

(56) References Cited

U.S. PATENT DOCUMENTS

| 4,681,454 A | 7/1987 | Breemer |
| 5,272,345 A * | 12/1993 | Durham ................. G01N 21/31 250/341.5 |

(Continued)

FOREIGN PATENT DOCUMENTS

| EP | 0152979 A1 | 8/1985 |
| JP | H06-201468 A | 7/1994 |

(Continued)

OTHER PUBLICATIONS

Bryant, "Photodiodes and other Light Sources", no date, pp. 1-18.*
(Continued)

*Primary Examiner* — Yelena G Gakh
(74) *Attorney, Agent, or Firm* — Roche Diagnostics Operations, Inc.

(57) ABSTRACT

An optical device for determining the presence and/or concentration of analytes in a sample is presented. The optical device comprises a detector and a detection unit comprising optical path components. The detection unit has wavelength-dependent responsivity. The optical device further comprises a light source for emitting light of different respective usable wavelength ranges. The light is guidable through the optical path to the detector to generate baseline signals and response signals relative to the baseline signal indicative of the presence and/or concentration of analytes in the optical path. The intensity of the light reaching the detector is adjusted inverse to the wavelength-dependent responsivity with respect to at least two respective usable wavelength ranges so that a reduction of the ratio between the maximum baseline signal at one of the selected usable wavelength ranges and the minimum baseline signal at another of the selected usable wavelength ranges is obtained.

8 Claims, 7 Drawing Sheets

(51) Int. Cl.
*G01J 3/28* (2006.01)
*G01J 3/42* (2006.01)
*G01N 21/25* (2006.01)

(58) Field of Classification Search
CPC .......... A61B 5/0075; A61B 2560/0214; A61B 5/1495; A61B 5/02427; A61B 1/043; A61B 5/0017; G01N 21/6428; G01N 33/48; G01N 2021/64
See application file for complete search history.

(56) References Cited

U.S. PATENT DOCUMENTS

| | | | | |
|---|---|---|---|---|
| 5,272,518 A | * | 12/1993 | Vincent | G01J 3/12 250/226 |
| 5,784,158 A | * | 7/1998 | Stanco | G01J 3/02 356/326 |
| 5,818,598 A | * | 10/1998 | Kebabian | 356/434 |
| 6,728,026 B2 | * | 4/2004 | Lee et al. | 359/337.11 |
| 2008/0094616 A1 | | 4/2008 | Tanaka | |
| 2008/0094631 A1 | | 4/2008 | Jung et al. | |

FOREIGN PATENT DOCUMENTS

| | | |
|---|---|---|
| JP | 2007-139632 A | 6/2006 |
| WO | 91/15992 A1 | 10/1991 |
| WO | 2005/031436 A1 | 4/2005 |

OTHER PUBLICATIONS

International Search Report dated Oct. 18, 2011 in Application No. PCT/EP2011/061677, 5 pages.

* cited by examiner

INCREASING THE USABLE DYNAMIC RANGE IN PHOTOMETRY

CROSS-REFERENCE TO RELATED APPLICATIONS

This application is a continuation of PCT/EP2011/061677, filed Jul. 8, 2011, which is based on and claims priority to EP 10170345.2, filed Jul. 21, 2010, which is hereby incorporated by reference.

BACKGROUND

The present disclosure generally relates to optical devices for determining the presence and/or concentration of analytes in a sample, comprising a detection unit having a wavelength-dependent responsivity and, in particular, to optical devices and methods for compensating the wavelength-dependent responsivity of the detection unit.

Several analyzers used in the analysis of samples, such as biological samples, comprise a light source to illuminate the sample and a photodetector to perform a photometric measurement. In clinical chemistry analyzers, for example, optical transmission through a cuvette containing a liquid sample is measured. The results are used to generate extinction data, which is the ratio between light intensity input and output through the sample. Optical extinction can be caused either by absorption or by scattering of the light in the sample. Both processes lead to a measurable extinction. In this way, the presence and/or concentration of analytes in a sample, which may be indicative of a diagnostic condition, can be determined by measuring response signals of the detector, typically at usable wavelengths. These are wavelengths at which the type of analytes being determined are typically absorbing or scattering light so that the smaller variations can be detected.

Typically, photodiodes are used as detectors due to their linearity of output current as a function of incident light, low noise, compact size and light weight, long lifetime, high quantum efficiency, and lower cost compared to photomultipliers. On the other side, the overall sensitivity of photodiodes compared to photomultipliers is lower, their area is small, there is no internal gain and the response time is usually slower. Thus, photodiode arrays are more typically used in order to allow higher speed parallel read out.

The material chosen to manufacture photodetectors operative in the visible wavelength range is normally silicon. Silicon is capable of generating significant photocurrent in a wavelength range comprised between about 190 and about 1100 nanometers, which is a usable range for the analysis of biological samples.

The response of a silicon-based photodetector versus wavelength of the incident light is however variable. In other words, the responsivity of the photodetectors is wavelength dependent. This means that provided the same light power would be input into the photodetector for the whole wavelength range, the measured signal or baseline signal would vary over the wavelength range following a curve, which resembles the curve of the responsivity.

The responsivity is defined as the ratio of generated photocurrent (A) to incident light power (W), typically expressed in A/W (Ampere/Watt). The responsivity may also be expressed as quantum efficiency, or the ratio of the number of photogenerated carriers to incident photons.

A "baseline signal" is defined as the signal derived from the conversion of electro-magnetic energy guided from a light source to the detector through an optical path without passing through a sample or with a sample being replaced by a blank or reference solution. The baseline signal is therefore a function of the light source intensity and photodetector responsivity at different wavelengths. In other words, the baseline signal at each selected usable wavelength range may be defined as a blank signal, any deviation from which is to be interpreted as an attenuation of signal caused by analytes present in the sample.

Moreover, it is not only the photodetector, which has a wavelength-dependent responsivity. Most of the components, which may be part of an optical path, such as lenses and dispersion elements have different properties at different wavelengths, so that the overall baseline signal is a function of several components used in a detection unit.

The wavelength-dependent responsivity is an inherent property of a detection unit, that the detector and at least some of the components of the optical path, typically all components which have an effect on the way light is transmitted, reflected, diffracted, refracted, scattered, etc., which may vary according to the wavelength used.

With reference to the detector, "inherent property" refers to the material inherent property, e.g. to the silicon wavelength-dependent responsivity of silicon-based detectors, which generate variable photocurrent in the wavelength range typical of the silicon material, as it is well known.

With reference to optical path components, the wavelength-dependent responsivity may be due to both material and the form, or geometry, of the components, e.g. material and geometry of a lens, material and space resolution of a grating, etc., which, at parity of light source intensity, may cause light of different wavelengths to reach the detector with different intensity. In extreme cases it may even block, or deviate, wavelengths out of a certain range in a manner that light of those wavelengths never reaches the detector.

Also a sample container itself being placed in the optical path may have a wavelength-dependent responsivity. For example, if glass or plastic cuvettes are used, it is known that these will absorb part of the radiation, e.g. in the ultraviolet range.

Also, currently used light sources, such as halogen lamps, have a variable intensity spectrum, which is lower at certain wavelengths, typically sloping down towards the ultraviolet (UV) and/or the infrared (IR) at the range boundaries and have a peak in the central part of the wavelength range, which is at about 700 nanometers.

Typically, in proximity of the boundaries of the range, especially in the UV range, when the relative intensity of the light source is lower, the responsivity of the detector is also lower, while when the relative intensity of the light source is higher, the responsivity of the detector is also higher. As a consequence, at parity of concentration, the response signal of an analyte being detected at a wavelength in proximity of the boundaries of the range may be too weak while the response signal of another analyte being detected at a wavelength where both the intensity of the light source and the responsivity of the detector are high may lead to signal saturation. For this reason, the dynamic range for the measurement is limited as the baseline signal is typically set according to the usable wavelength where the relative intensity of the light source and the responsivity of the detector are lowest. This is done so that small concentrations of an analytes can be measured.

This however means that a very broad dynamic range for the detector is needed while the usable dynamic range is small. This, in some cases, may result in the need to dilute a sample being analyzed and repeat the measurement if the measured extinction was too high.

Photodiode arrays with a preamplifier for each pixel are normally used to best deal with this problem, at the expense however of complexity and cost. An alternative way would be to vary the integration time at different wavelengths but this method is not suitable when fast measurements are needed.

Therefore, there is a need to provide an optical device, which is simple and cost efficient and which is less dependent on the dynamic range of the detector.

SUMMARY

According to the present disclosure, an optical device for determining the presence and/or concentration of analytes in a sample is presented. The optical device can comprise a detection unit comprising optical path components and a detector. The detection unit can have a wavelength-dependent responsivity ($Rdu(\lambda)$). The optical device can further comprise a light source comprising at least two light emitting elements for emitting light of different respective usable wavelength ranges. Light from the light source can be guidable through an optical path to the detector to generate baseline signals at the respective usable wavelength ranges and to generate response signals relative to the baseline signals when a sample is located in the optical path. The response signals can be indicative of the presence and/or concentration of analytes in the sample. The intensity of at least a first and a second light emitting elements can be inverse to the wavelength-dependent responsivity ($Rdu(\lambda)$) of the detection unit with respect to at least a first and a second usable wavelength ranges respectively. The responsivity of the detection unit can be higher at the first usable wavelength range than at the second usable wavelength range, so that the ratio between the first baseline signal at the first usable wavelength range and the baseline signal at the second usable wavelength range can be less than the ratio between the responsivity of the detection unit at the first usable wavelength range and the responsivity of the detection unit at the second usable wavelength range.

In accordance with one embodiment of the present disclosure, at least one light regulator can be located in the optical path to compensate the wavelength-dependent responsivity ($Rdu(\lambda)$) of the detection unit with respect to at least a first and a second usable wavelength ranges respectively.

Accordingly, it is a feature of the embodiments of the present disclosure to provide an optical device, which is simple and cost efficient and which is less dependent on the dynamic range of the detector. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
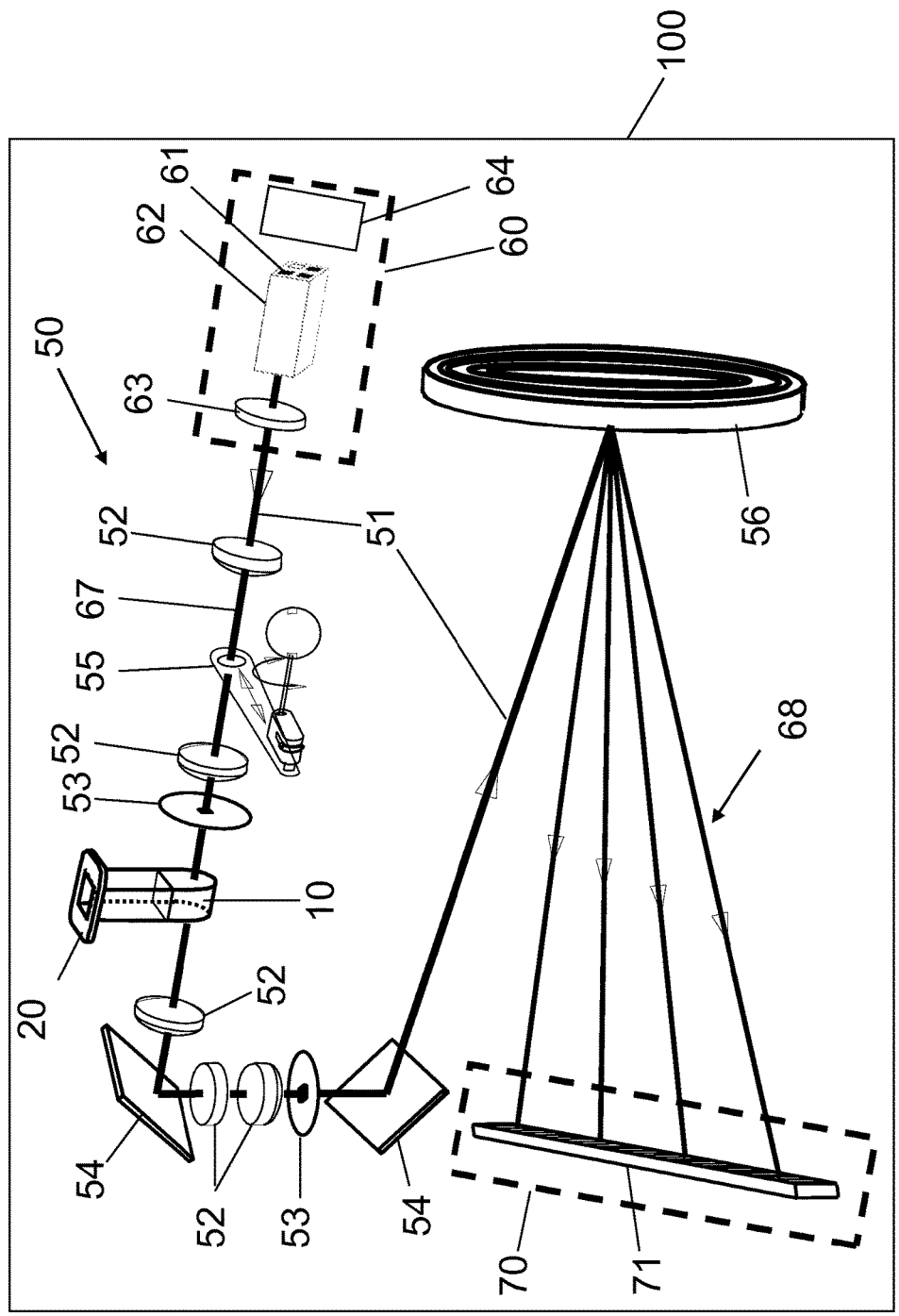
FIG. 1 illustrates schematically an optical device for determining the presence and/or concentration of analytes in a sample being located in the optical path according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present An "optical device" can be either a self-standing instrument or an integrated component within an analyzer or a module within an analytical system, suitable for the optical analysis of analytes present in a sample and particularly for measuring the optical transmission through a sample. The optical device can particularly be suitable for analyzing biological samples. Samples can be liquid solutions in which one or more analytes of interest can be potentially found, such as, for example, body fluids like blood, serum, plasma, urine, milk, saliva, cerebrospinal fluid, or any other suitable fluid. Samples may be analyzed as such or after being diluted with another solution or after having being mixed with reagents for example to carry out one or more diagnostic assays like, for example, clinical chemistry assays and immunoassays. Thus the optical device may advantageously be used to detect the result of a chemical or biological reaction or to monitor the progress of a chemical or biological reaction, such as, for example, in a coagulation assay, agglutination assay, or turbidimetric assay. Other diagnostic assays can include for example the qualitative and/or quantitative analysis of analytes such as albumin, ALP, Alanine Aminotransferase, Ammonia, Amylase, Aspartat Aminotransferase, Bicarbonate, Bilirubin, Calcium, Cardiac Markers, Cholesterol, Creatinine Kinase, D-Dimer, Ethanol, g-Glutamyltransferase, Glucose, HBA1c, HDL-Cholesterol, Iron, Lactate, Lactate Dehydrogenase, LDL-Cholesterol, Lipase, Magnesium, Phosphorus inorganic, Potassium, Sodium, Total Protein, Triglycerides, UREA, Uric Acid and any other suitable analysis.

The "detection unit" can be a system within the optical device comprising optical path components and a detector, which can make it possible to guide light through a sample in a controlled manner and to measure optical transmission, such as absorption and/or scattering or reflection. The detection unit may be however carry out any other spectroscopic measurement. It may also entail temporally static measurements, time resolved measurements, or both.

The optical path may comprise components such as lenses, minors, apertures, filters, a shutter, a heat shield, fiber optics, a dispersion element, or any other suitable components. A dispersion element may be a transmission or reflection diffraction grating, and may be a scanning monochromator or a polychromator, which can receive transmitted light and disperse it into multiple spectral components. A dispersion element may be also a refractive element, such as a prism.

A "detector" can be an optical detector or photodetector, which can be a device that converts electro-magnetic energy into an electrical signal, including both single element and multi-element or array optical detectors. Thus an optical detector can be a device capable of monitoring an optical electro-magnetic signal and providing an electrical output signal or response signal relative to a baseline signal indicative of the presence and/or concentration of an analyte in a sample located in the optical path. Such devices can include, for example, photodiodes, including avalanche photodiodes, phototransistors, photoconductive detectors, linear sensor arrays, CCD detectors, CMOS optical detectors, including CMOS array detectors, photomultipliers, and photomultiplier arrays. According to some embodiments, an optical detector, such as a photodiode or photomultiplier, may contain additional signal conditioning or processing electronics. For example, an optical detector may include at least one pre-amplifier, electronic filter, or integrating circuit. Suitable pre-preamplifiers can include integrating, transimpedance, and current gain (current mirror) pre-amplifiers. According to one embodiment, the detector can be a CCD or CMOS detector. According to another embodiment, the detector can be a photodiode or PMT.

A light source can be a unit within the optical device comprising at least one light emitting element capable of emitting usable light. The term "usable" can refer to a selected wavelength or wavelengths or to a wavelength range or ranges within a broader wavelength range, at which wavelength(s), light guided through a sample can be used to measure with sufficient sensitivity small variations in analyte concentrations present in a sample and/or minimum concentrations relative to a baseline signal. Of course, the at least one light emitting element may emit light in a non-usable range as far as it emits light in at least one usable range. Also, the term usable is intended as a relative term, in the sense that a certain wavelength range may be usable to measure one or a group of analytes, while for other analytes it may be less usable, which can mean that it can still be used also for other analytes if a loss of sensitivity is accepted. On the other hand if optimal measurement conditions are required, a different usable wavelength range may need to be selected.

The term "wavelength range" can be interpreted in a broad manner including both narrow ranges, for example, of a few nanometers such as about 2-20 nanometers, and broader ranges, such as, for example of about 20-100 nanometer or more. It is also to be understood that ranges may be at least in part overlapping.

A "light emitting element" can be an electric powered radiation source such as for example an incandescent lamp, an electroluminescent lamp, a gas discharge lamp, a high-intensity discharge lamp, a laser and the like.

According to one embodiment, the at least one light emitting element can be for example a halogen lamp, which like all incandescent light bulbs, can produce a continuous broad spectrum of light, from near ultraviolet to deep infrared.

According to one embodiment, the at least one light emitting element can be a light emitting diode. The term "light emitting diode" or "LED" can be used herein to refer to conventional light-emitting diodes, that is, inorganic semiconductor diodes that convert applied electrical energy to light. Such conventional LEDs can include, for example, aluminum gallium arsenide (AlGaAs), which can generally produce red and infrared light, gallium aluminum phosphide, which can generally produce green light, gallium arsenide/phosphide (GaAsP), which can generally produce red, orange-red, orange, and yellow light, gallium nitride, which can generally produce green, pure green (or emerald green), and blue light, gallium phosphide (GaP), which can generally produce red, yellow and green light, zinc selenide (ZnSe), which can generally produce blue light, indium gallium nitride (InGaN), which can generally produce bluish-green and blue light, indium gallium aluminum phosphide, which can generally produce orange-red, orange, yellow, and green light, silicon carbide (SiC), which can generally produce blue light, diamond, which can generally produce ultraviolet light, and silicon (Si), which are under development. The LEDs may not be limited to narrowband or monochromatic light LEDs; LEDs may also include broad band, multiple band, and generally white light LEDs.

The term LED can also be used herein to refer to Organic Light Emitting Diode (OLED), that can be polymer-based or small-molecule-based (organic or inorganic), edge emitting diodes (ELED), Thin Film Electroluminescent Devices (TFELD), Quantum dot based inorganic "organic LEDs," and phosphorescent OLED (PHOLED).

Thus, according to some embodiments, the LED can be a standard semiconductor device, an organic LED, or an inorganic LED. Examples of organic LEDs can be QDOT-based LEDs and nanotube-based LEDs. The LED can be a stack of LED's such as a stack of organic LEDs or a stack of organic LED layers.

According to one embodiment, the light source can comprise a plurality of light emitting elements with different respective usable wavelengths or wavelength ranges. For example, the light source can comprise a combination of two, three, or more LEDs, such as, for example having a first usable relatively short wavelength spectrum (e.g., UV-blue) LED, a second usable "redder" or longer wavelength spectrum LED, a third usable even redder or longer wavelength spectrum LED and so on up to eventually the infrared wavelengths depending on the number and type of usable wavelengths needed.

Each LED may be configured to generate for example between about 500 μW and about 1 W of emission energy. Alternatively or in combination, some LEDs of the array may be configured to generate a low emission energy, some a medium emission energy, and some a high emission energy.

The light source may comprise a cooling device such as a heat sink or fan to take away the heat generated by the light emitting element(s) and to prevent fluctuations of illumination and/or spectral shifts.

The light source and the optical path components can be configured so that light from the light source can be guided through an optical path to the detector to generate baseline signals at the respective usable wavelength ranges and to generate response signals relative to the baseline signals when a sample is located in the optical path, the response signals being indicative of the presence and/or concentration of analytes in the sample. The sample may be located for example in a cuvette, flow-through cell, or the like, in the optical path.

According to some embodiments, the optical device can comprise a light mixing element consisting of light shaping and homogenizing optics, such as for example a mixing rod, for homogenizing the light emitted by the plurality of light emitting elements and improving illumination uniformity before illuminating a sample located in the optical path. The light mixing element may be a component of the optical path or of the light source.

According to one embodiment, the light source can comprise a plurality of light emitting elements, such as, for example, at least two light emitting elements. In particular, the intensity of at least a first light emitting element and a second light emitting element can be adjusted in a manner inverse to the wavelength-dependent responsivity of the detection unit with respect to at least a first and a second usable wavelength ranges respectively, the responsivity of the detection unit being higher at the first usable wavelength range than at the second usable wavelength range. In this way, a ratio between the first baseline signal at the first usable wavelength range and the baseline signal at the second usable wavelength range can be obtained, which can be less than the ratio between the responsivity of the detection unit at the first usable wavelength range and the responsivity of the detection unit at the second usable wavelength range.

In mathematical terms, the baseline signal $BL(\lambda)$ is the spectrum of the light source $S(\lambda)$ as a function of the wavelength $\lambda$, times the detector responsivity $Rd(\lambda)$, which is also a function of the wavelength $\lambda$, times the optical path responsivity $Rop(\lambda)$, which is also a function of the wavelength $\lambda$. The formula can thus be written as $BL(\lambda)=S(\lambda)*Rd(\lambda)*Rop(\lambda)$. This can be abbreviated by as $BL(\lambda)=S(\lambda)*Rdu(\lambda)$ wherein $Rdu(\lambda)$ is the responsivity of the detection unit, which corresponds to $Rd(\lambda)*Rop(\lambda)$. $S(\lambda)$ is expressed in Watt (W). $Rdu(\lambda)$ is expressed in Ampere/Watt (A/W). $BL(\lambda)$ is thus expressed in Ampere (A), which is the current measured by the detector and converted into a baseline signal.

The level of the baseline signal can be variable in a wavelength-dependent manner according to the above formula. This can mean that, in a set of selected usable wavelength ranges, there can be a wavelength range at which the baseline can have a maximum level and one at which it can have a minimum level. It can therefore be possible to normalize the baseline signals at all selected usable wavelengths by dividing for the maximum baseline signal. Thus, the maximum baseline line can be given a 100% value, while all other can be expressed as a fraction, or percent, of the maximum baseline signal. The ratio between maximum and the minimum baseline signal among the selected wavelength ranges can define the dynamic range of the baseline signal.

Adjusting the intensity of light emitting elements to compensate for the wavelength-dependent responsivity of the detection unit, in a manner inverse to the wavelength-dependent responsivity of the detection unit, can mean that the light source can be configured such that individual light emitting elements can emit light with an intensity, which can be higher where the responsivity of the detection unit is lower and can be lower where the responsivity of the detection unit is higher respectively, at least with respect to selected usable wavelengths. This can mean that by selecting, for example, a first and a second wavelength range, $\lambda 1$ and $\lambda 02$ respectively, the responsivity of the detection unit being higher at the first usable wavelength range than at that second usable wavelength range, that is, $Rdu(\lambda 1)>Rdu(\lambda 2)$, the intensity of a light source $S(\lambda 2)$, that is, of a second light emitting element emitting light in that second wavelength range can be increased compared to the intensity of a first light source $S(\lambda 1)$, that is of a first light emitting element emitting light in the first wavelength range. In particular, the formula for $\lambda 1$ is $BL(\lambda 1)=S(\lambda 1)*Rdu(\lambda 1)$. The formula for $\lambda 2$ is $BL(\lambda 2)=S(\lambda 2)*Rdu(\lambda 2)$. The relation between $\lambda 1$ and $\lambda 2$ is given by the formula $BL(\lambda 1)/BL(\lambda 2)=S(\lambda 1)/S(\lambda 2)*Rdu(\lambda 1)/Rdu(\lambda 2)$. If $S(\lambda 1)$ was equal to $S(\lambda 2)$ then the ratio between $BL(\lambda 1)$ and $BL(\lambda 2)$ can be equal to the ratio between $Rdu(\lambda 1)$ and $Rdu(\lambda 2)$.

Obtaining a ratio between a first baseline signal at a first usable wavelength range and a baseline signal at a second usable wavelength range, which can be about 50% or less of the ratio between the responsivity of the detection unit at the first usable wavelength range and the responsivity of the detection unit at the second usable wavelength range, can mean adjusting the intensity of a second light emitting element $S(\lambda 2)$ relative to that of a first light emitting element $S(\lambda 1)$ such that $BL(\lambda 1)/BL(\lambda 2)*Rdu(\lambda 2)/Rdu(\lambda 1)$ can be about 0.5 or less. In another embodiment, it can be less than about 0.1, or 10%. By adjusting $S(\lambda 1)$ and $S(\lambda 2)$ inversely proportional to $Rdu(\lambda 1)$ and $Rdu(\lambda 2)$ respectively, a baseline $BL(\lambda 1)$ can be obtained for $\lambda 1$, which can be the same as the baseline $BL(\lambda 2)$ for $\lambda 2$, that is $BL(\lambda 1)/BL(\lambda 2)=1$.

$S(\lambda n)$ wherein $\lambda n$ stands for any selected wavelength range can be adjusted so that the dynamic range of the baseline signal, which can be the ratio between the maximum baseline signal $BL(\lambda max)$ and the minimum baseline signal $BL(\lambda min)$ among the selected wavelength ranges can be reduced by at least 50%, in another embodiment, at least about 90% up to 100% compared to a baseline generated by a light source, which can be constant at all wavelength ranges. In other words, $BL(\lambda max)/BL(\lambda min)*Rdu(\lambda min)/Rdu(\lambda max)$ can be about 0.5 or less, or in another embodiment less than about 0.1. By adjusting $S(\lambda n)$ inversely proportional to Rdu(λn), a baseline BL(λn) can be obtained which can be the same at any selected wavelength.

Adjusting the intensity of light emitting elements to compensate for the wavelength-dependent responsivity of the detection unit can contribute also to minimize the often encountered and undesired problem of stray light. "Stray light" can be defined as light in the optical device, particularly in the detection unit, which can reach the detector at wavelengths (λn) other than the one(s) intended. As a result, the base signal and/or the response signal generated by detector may not be due only to light of wavelength λn as intended but also to light of wavelength other than λn, which may not be intended, thus producing an error, that is, a deviation from the correct signal, which can bias the measurement. This error due to stray light can be negligible as far as the signal due to the intended light can be much larger than the signal due to stray light. However, where the responsivity of the detector is lower at an intended wavelength and higher at one or more wavelengths other that the intended wavelength, the error due to stray light may be significant. The effect of stray light may be even more severe when in addition to a lower responsivity at the intended wavelength compared to non-intended wavelengths, the intensity of the light of the intended wavelength can be lower than that of light of non-intended wavelengths. Therefore compensating for the wavelength-dependent responsivity of the detection unit according to the invention can reduce also possible errors due to stray light.

According to one embodiment, at least for one or more wavelengths where the stray light problem is more significant, the intensity of the respective light emitting elements can be further adjusted, that is, further increased compared to the intensity of the other light emitting elements emitting light in other usable wavelength ranges and/or the intensity of the light emitting elements emitting light in the other usable wavelength ranges may be further decreased. This can mean that, by selecting for example a first and a second wavelength range, λ1 and λ2 respectively, the responsivity of the detection unit being higher at the first usable wavelength range than at the second usable wavelength range, that is, Rdu(λ1)>Rdu(λ2), the intensity of the second light emitting element S(λ2) may be increased compared to the intensity of the first light emitting element S(λ1) and/or the intensity of the first light emitting element S(λ1) may be decreased compared to that of the second light emitting element S(λ2) such that BL(λ1)/BL(λ2)<1.

Adjusting the intensity of light emitting elements can be achieved for example by varying the electrical power input for individual light emitting elements, for example, by providing more electrical power input to the light emitting elements which can emit light of usable wavelengths or wavelength ranges at which the responsivity of the detection unit can be lower and optionally by providing less electrical power input to the light emitting elements which can emit light of usable wavelengths or wavelength ranges at which the responsivity of the detection unit can be higher. It may be sufficient to adjust the intensity of only one light emitting element for a selected usable wavelength range, for example, where the responsivity of the detection unit can be lower. Typically, the closer the selected usable wavelength ranges are, the smaller is the difference in the value or level of the respective baseline signals, which can mean that it can be less important to compensate for this difference. Thus adjusting the intensity of at least two light emitting elements can have to be interpreted in a relative manner, which can include setting or fixing the intensity of a first light emitting element and adjusting the intensity of a second light-emitting element relative to the intensity of the first light emitting element, irrespective of whether the first light emitting element can be used for that particular analysis. Alternatively, since the wavelength-dependent responsivity can be an inherent property of the detection unit, different light emitting elements of respectively different energy power according to the emission wavelength can be used.

Depending on the nature of the light emitting elements, the number of the light emitting elements and the emission wavelengths, either a continuous broadband emission spectrum comprising usable wavelengths or discrete narrow emission spectra comprising selected usable wavelengths can be generated. Consequently also the baseline signal may be either continuous or discontinuous with signal zones for each of the selected usable wavelengths and gaps in between. The light source can be also configured such that only selected light emitting elements, for example, those emitting light usable to detect selected analytes can be turned on or used while the others may remain off.

Ideally, a baseline signal for each of the selected usable wavelengths can be obtained, which can be nearly flat and/or nearly at the same level, wherein the dynamic range can be about 1. In practice, however, any reduction in the baseline signal variation can bring considerable advantages, since this can increase an equal amount of the available dynamic range for the measurement.

The dynamic range of an analyte can be defined as the range of concentrations, which can be typical for that analyte in a sample. The dynamic range of the detector can be defined as the ratio between the maximum detectable light at or near saturation and the lowest detectable light, which can typically be limited by the noise level. The dynamic range of the baseline signal can be defined as the ratio between the maximum baseline signal BL(λmax) and the minimum baseline signal BL(λmin) for a set of selected usable wavelength ranges. The available dynamic range for the measurement can be the dynamic range which can be effectively used for detection, in other words the usable dynamic range. This can be defined as the ratio between the maximum detectable change in concentration of analyte and the minimum detectable change in concentration of analyte, which can be limited by BL(λmin). The usable dynamic range can thus be the dynamic range of the detector minus the dynamic range of the baseline signal. It can thus be smaller than the dynamic range of the detector. The dynamic range of the analyte may thus exceed the available dynamic range for the measurement, meaning that the highest concentrations of analyte may not be measurable. That can be why it can be important to reduce the dynamic range of the baseline signal.

In order to get closer to the ideal status, electronic compensation on the detector side, for example by pre-amplifiers or electronic filters, can also be combined with the compensation of light intensities.

According to another embodiment, in order to compensate the wavelength-dependent responsivity of the detection unit at least with respect to selected usable wavelengths such that a ratio between the first baseline signal at the first usable wavelength range and the baseline signal at the second usable wavelength range can be obtained, which can be less than, about 50% or less of, the ratio between the responsivity of the detection unit at the first usable wavelength range and the responsivity of the detection unit at the second usable wavelength range, at least one light regulator can be located in the optical path.

A light regulator can be an optical element which can enable the reduction of the amount of light reaching the detector at least with respect to selected wavelengths. A light regulator may be for example a light filter or an obscuring object such as a slit or diaphragm.

The light filter may be a patterned filter, for example, a hybrid filter comprising a multi-band filter over a patterned filter layer, or may comprise multiple filters, for example, an array or stack of filters, for different wavelengths to compensate the wavelength-dependent responsivity of the detection unit at least with respect to selected usable wavelengths. This can mean that light can be dimmed at those wavelengths where the responsivity of the detection unit is higher, that is in a manner inverse to the responsivity of the detection unit at least with respect to selected usable wavelengths.

The light regulator may be mounted over the detector, for example, covering at least in part the detector sensor surface. Alternatively, the light regulator may be coupled to the light source to cover at least in part the light emitting element, or be a component of the optical path.

The light source may be a broadband light source, for example, comprising one broadband light emitting element. The light source may however comprise a plurality of light emitting elements with narrow- or broad-band emissions.

The light regulator compensation may be combined with compensation of light intensities and/or with electronic compensation so that a baseline signal for each of the selected usable wavelengths can be obtained with even less variation.

An analyzer for determining the presence and/or concentration of analytes in samples can comprise the optical device. An analyzer can be an apparatus assisting users with the detection, for example, qualitative and/or quantitative optical evaluation of samples for diagnostic purpose. Examples of such an analyzer can be a clinical chemistry analyzer, a coagulation chemistry analyzer, an immunochemistry analyzer, a urine analyzer, either as self-standing instruments or modules within a system comprising a plurality of the modules, used to detect the result of chemical or biological reactions or to monitor the progress of chemical or biological reactions or any other suitable analyzer.

The analyzer may comprise units assisting with the pipetting, dosing, and/or mixing samples and/or reagents, units for loading and/or unloading and/or transporting and/or storing sample tubes or racks comprising sample tubes, units for loading and/or unloading and/or transporting and/or storing reagent containers or cassettes and the like. The analyzer may also comprise identification units comprising sensors, for example, barcode readers. Alternative technologies such as RFID may also be used for identification.

A pipetting unit may comprise a reusable washable needle, for example, a steel needle, or disposable pipette tips. Typically, the pipetting unit can be operatively coupled to an automated positioning device for moving the pipette tip or needle with respect to the analytical device and, for example, may be mounted to a transfer head that can be moved in two directions of travel in a plane, for example, by guiding rails and a third direction of travel orthogonal to the plane, for example, by a spindle drive.

The analyzer may also comprise a cuvette handling unit for transporting cuvettes comprising samples, including reaction mixtures, to be analyzed into a detection position located in the optical path of the detection unit. The cuvette handling unit may be a conveyor, for example, a linear or rotor like conveyor, moving in at least one direction or as a robotic arm capable of performing translation movements along one or more of possible orthogonal axis, driven by one or more electrical motors. According to one embodiment, the cuvette handling unit can comprise several cuvette sections for receiving and transporting at least one cuvette at a time into at least one detection position.

According to one embodiment, the optical path may comprise a plurality of detection positions to receive a plurality of cuvettes, for analyzing a plurality of samples in parallel.

According to one embodiment, the analyzer can comprise a plurality of optical devices.

The analyzer may further comprise incubation units for maintaining sample/reagent mixtures at a certain temperature during reaction, wash stations for washing pipette tips or needles, mixing paddles, and the like.

The analyzer can comprise a controller for controlling the automated analysis of samples according to a predetermined process operation plan which, for example, may be embodied as programmable logic controller running a computer-readable program provided with instructions to perform operations in accordance with the process operation plan.

The term "relative to a baseline signal" can be used to mean any deviations from the baseline signal due to the sample being analyzed, which can be either above or below the baseline signal, typically below as transmission values are recorded as extinction.

According to one embodiment, adjusting the intensity of light emitting elements can comprise adjusting the level of the baseline signal so that the dynamic range of the detector can comprise the dynamic range of the analyte concentrations being determined, at least with respect to selected usable wavelengths. This can mean that at least with respect to selected usable wavelengths, the light intensity of the light emitting elements emitting light at those wavelengths can be adjusted so that the baseline signal can be near the saturation limit of the detector. In this way, the full dynamic range of the detector until the limit of detection of the detector can be used to determine the concentration of analytes without the need to eventually dilute the sample if the concentration of the analyte is too high. For example if a detector, for example, a CCD or CMOS detector, is used, the dynamic range of this detector type can typically be about 1000:1. If the intensity of the light emitting elements is not adjusted such as to compensate the wavelength-dependent responsivity of the detection unit, the available dynamic range for determining analyte concentrations throughout the usable wavelength range can be reduced below about 4:1, since a considerable portion of this dynamic range can be used up by the baseline, thus making these detectors not suitable for detecting changes in analyte concentrations which may be in the order of about 1000:1. Thus, by compensating the wavelength-dependent responsivity of the detection unit, the usable dynamic range for measurement can be maximized by nearly covering the dynamic range of the detector, thus enabling the use of detectors with smaller dynamic range, which can mean the use of cheaper detectors. Of course detectors such as photodiode arrays and photomultiplier tubes may still be used, wherein the available dynamic range for the measurement can be even greater, thus enabling detection of analytes in a broader concentration range, without the need, for example, to dilute the sample for highly concentrated samples.

According to one embodiment, adjusting the level of the baseline signal can be carried out as a function of the type of sample or of type of analytes being determined, meaning that the baseline signal may be adjusted for individual usable wavelengths or ranges according to the analytes being detected and/or according to the expected dynamic range typical of samples and/or analytes present in the samples. It may be, for example, also possible to shift the baseline signal towards the central part of the detector dynamic range to be sufficiently far from the saturation limit and from the limit of detection of the detector in case low analyte concentrations or small concentration changes can be expected. In other words, it can be possible not only to adjust the level of the baseline signal so that the dynamic range of the detector can comprise the dynamic range of the analyte concentrations being determined, but also to place the baseline signal at an optimum level within this range, for example, by centering the dynamic range of the analyte concentrations with respect to the center of the dynamic range of the detector, at least with respect to selected usable wavelengths.

According to some embodiments, compensating at least in part the wavelength-dependent responsivity of the detection unit at least with respect to selected usable wavelengths by at least one light regulator located in the optical path, that is, by combining the compensation achieved by adjusting the intensity of the light source with the compensation achieved by a light regulator. Compensation achieved by adjusting the intensity of the light source and/or with the compensation can be achieved by a light regulator can be still further combined with electronic compensation in order to achieve even lower variations of the baseline signal.

According to one embodiment, a ratio between the first baseline signal at the first usable wavelength range and the baseline signal at the second usable wavelength range can be obtained, which can be less than about 10% of the ratio between the responsivity of the detection unit at the first usable wavelength range and the responsivity of the detection unit at the second usable wavelength range.

Referring initially to FIG. 1, a schematically depiction of an optical device 100 for determining the presence and/or concentration of analytes in a sample 10 comprised in an optical cuvette 20 located in the optical path 51 of a detection unit 50 is illustrated. The detection unit 50 can comprise optical path components such as lenses 52, apertures 53, mirrors 54, a shutter 55, and a diffraction grating 56, which can receive light 67 transmitted through the sample 10 and can disperse it into multiple spectral components 68. The detection unit 50 can further comprises an optical detector 70, comprising an array optical sensor 71 such as CCD sensor, which can convert electro-magnetic energy from light 68 into an electrical signal. The sensor 71 can be divided in sectors, each of which can be dedicated to a usable wavelength range. The optical device 100 can further comprise a light source 60 comprising an array of light emitting elements, such as LEDs 61, for emitting light of different respective usable wavelength ranges, wherein light from the LEDs can be mixed by a mixing rod 62 and can be guided through the optical path 51 to the detector 70 to generate a response signal relative to a baseline signal indicative of the presence and/or concentration of analytes in the sample 10. The light source can further comprise a heat shield 63 to shield the heat from entering the detection unit 50 and a heat sink 64 to take away the heat generated by the LEDs 61. The direction of the light is indicated by arrows along the optical path 51.

The light source 60 can be configured such that the intensity of the light emitted by the individual LEDs 61 can be adjusted in a manner reciprocal to the wavelength-dependent responsivity of the detection unit 50 at those respective wavelengths, the wavelength-dependent responsivity depending both on the optical components and the detector sensor 71. By this compensation, a reduction of the ratio between the maximum baseline signal at one of the selected usable wavelength ranges and the minimum baseline signal at another of the selected usable wavelength ranges can be obtained. In other words, a reduction of the baseline dynamic range can be obtained.

Figure 2:
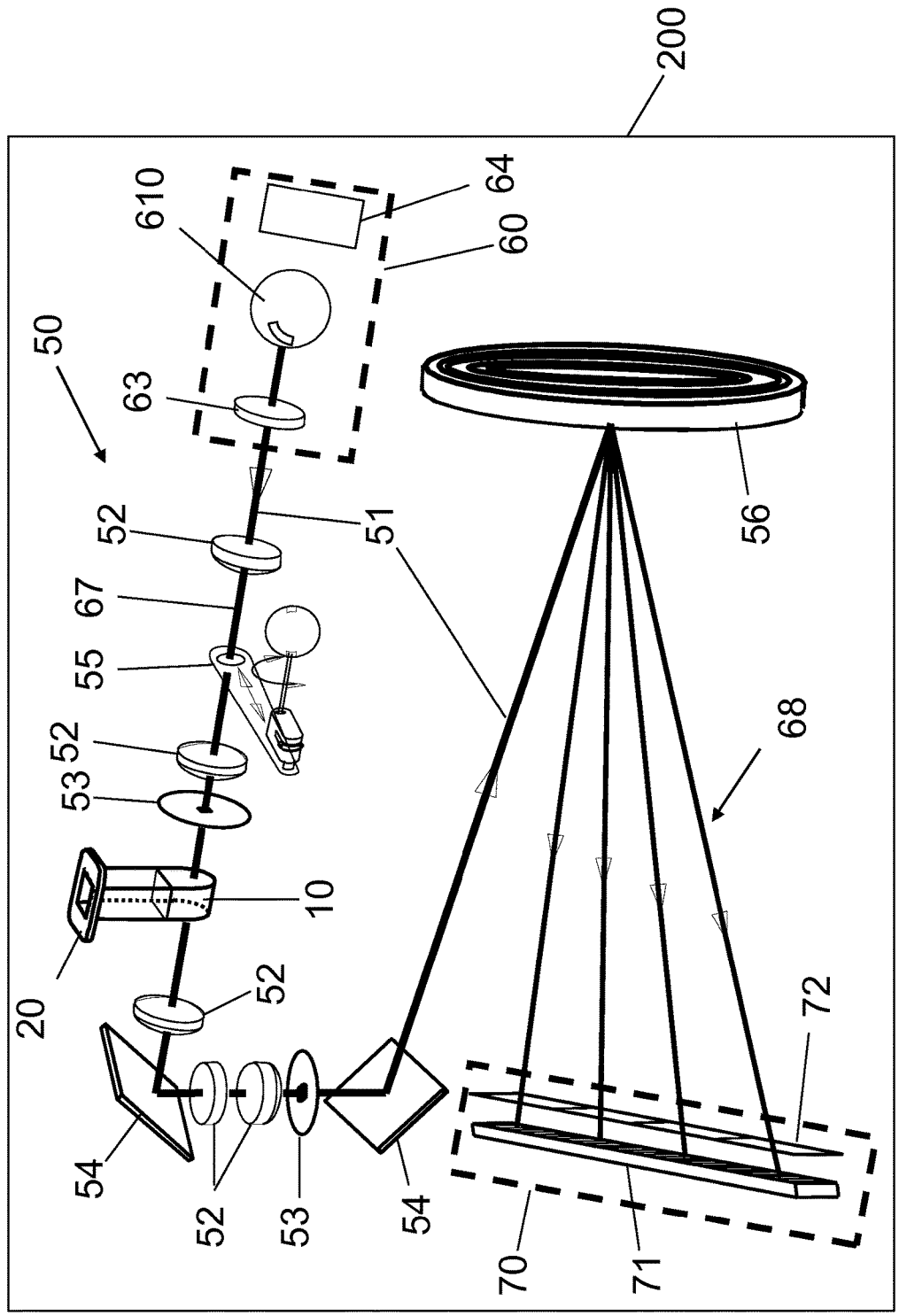
FIG. 2 illustrates schematically another optical device for determining the presence and/or concentration of analytes in a sample being located in the optical path according to an embodiment of the present disclosure.

FIG. 2 depicts schematically another optical device 200 for determining the presence and/or concentration of analytes in a sample 10 comprised in an optical cuvette 20 located in the optical path 51 of the detection unit 50. Since most of the features of this embodiment are in common with that of FIG. 1, only the differences will be explained. In particular, the light source 60 can comprise one light emitting element, for example, a halogen lamp, which can emit light in a broad usable wavelength range. The optical device 200 can also comprise a light regulator 72 located in the optical path to compensate for the wavelength-dependent responsivity of the detection unit at least with respect to selected usable wavelength ranges. In this example, the light regulator 72 can be a patterned obscuring filter extending over the surface of the detector sensor 71. The light regulator 72 can dim the light reaching the sensor 71 at those wavelengths where the responsivity of the detection unit 50 can be higher and with a degree inversely proportional to the responsivity of the detection unit 50 at least with respect to selected usable wavelengths.

Figure 3A:
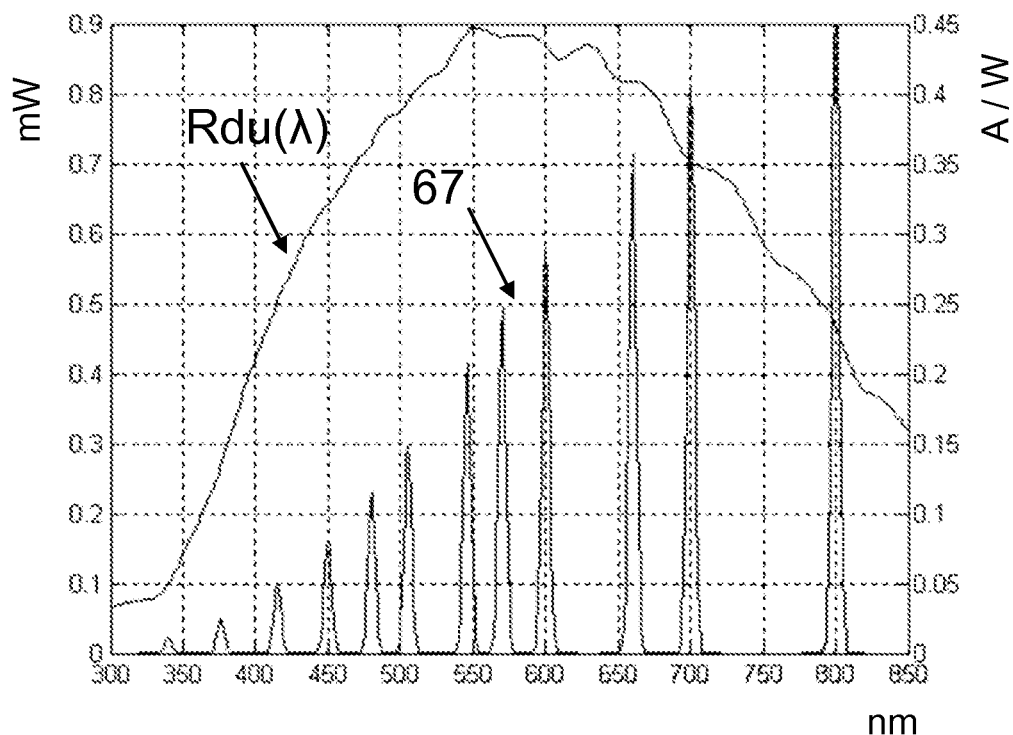
FIG. 3a illustrates, on the same graph, the wavelength dependent responsivity typical of state of the art detection units as well as the wavelength dependent intensity typical of state of the art broad spectrum light sources, mimicked with a plurality of light emitting elements each emitting light in a usable wavelength range.
Figure 3B:
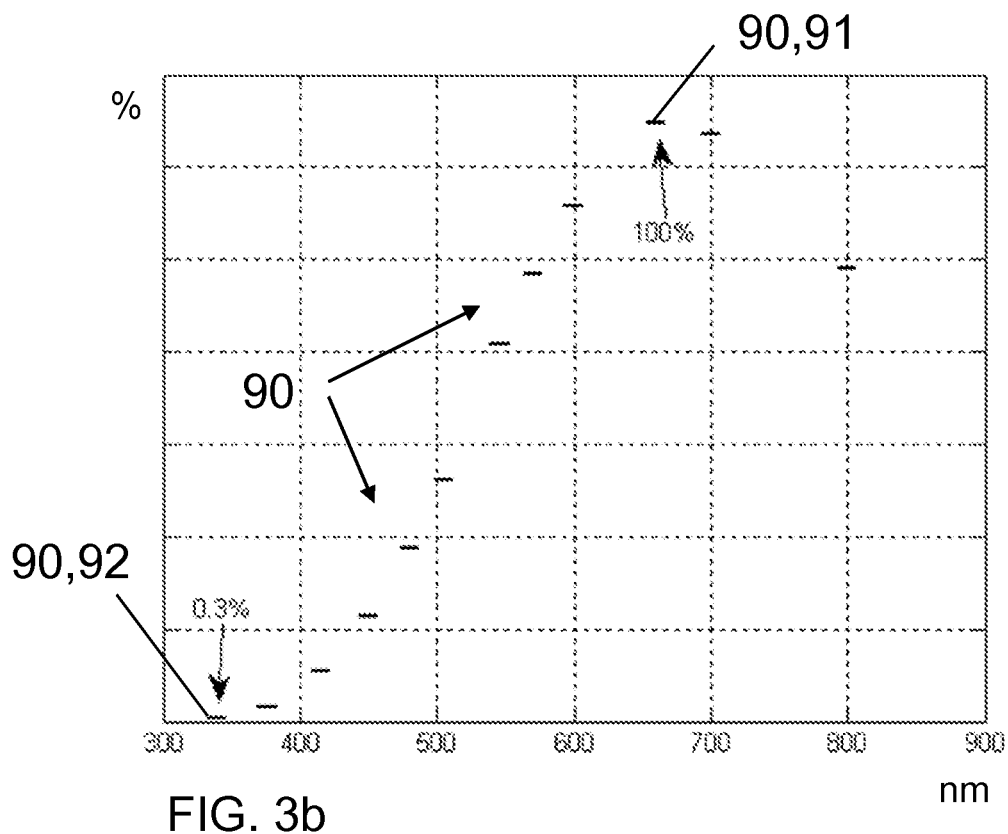
FIG. 3b illustrates the state of the art baseline signal at each of the usable wavelength ranges of FIG. 3a as a function of the wavelength dependent responsivity of the detection unit and the intensity of the light source at that respective wavelength.
Figure 4A:
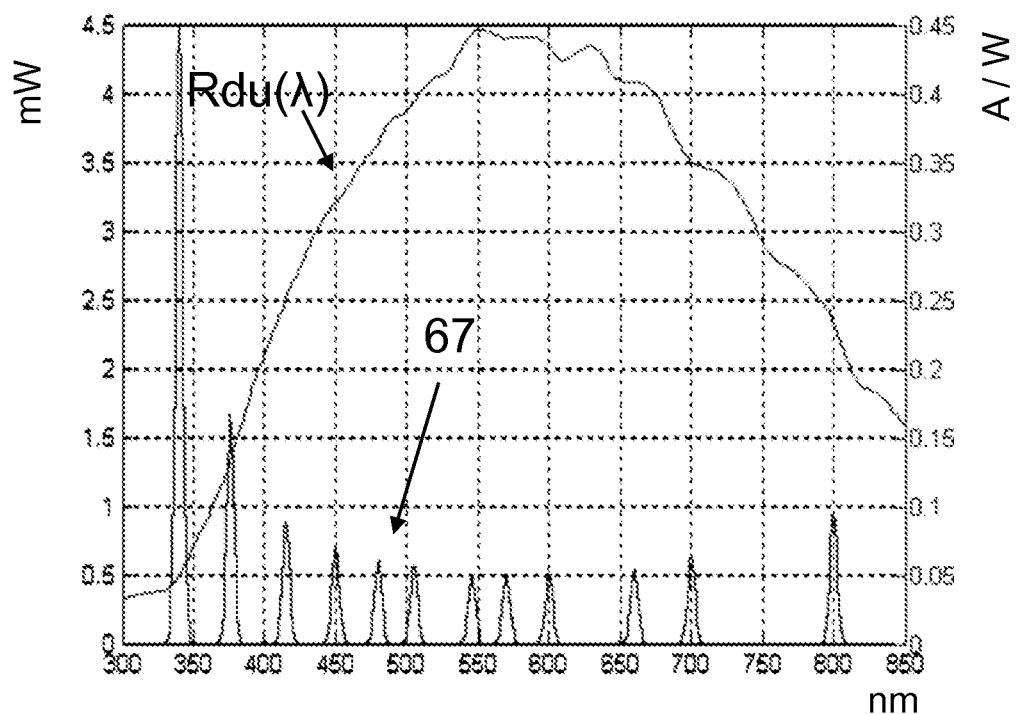
FIG. 4a illustrates on the same graph the wavelength dependent responsivity of the detection unit as well as the intensity of light for each of a plurality of light emitting elements emitting light in respective usable wavelength ranges, wherein the intensity is adjusted in a manner reciprocal to the wavelength-dependent responsivity of the detection unit according to an embodiment of the present disclosure.
Figure 4B:
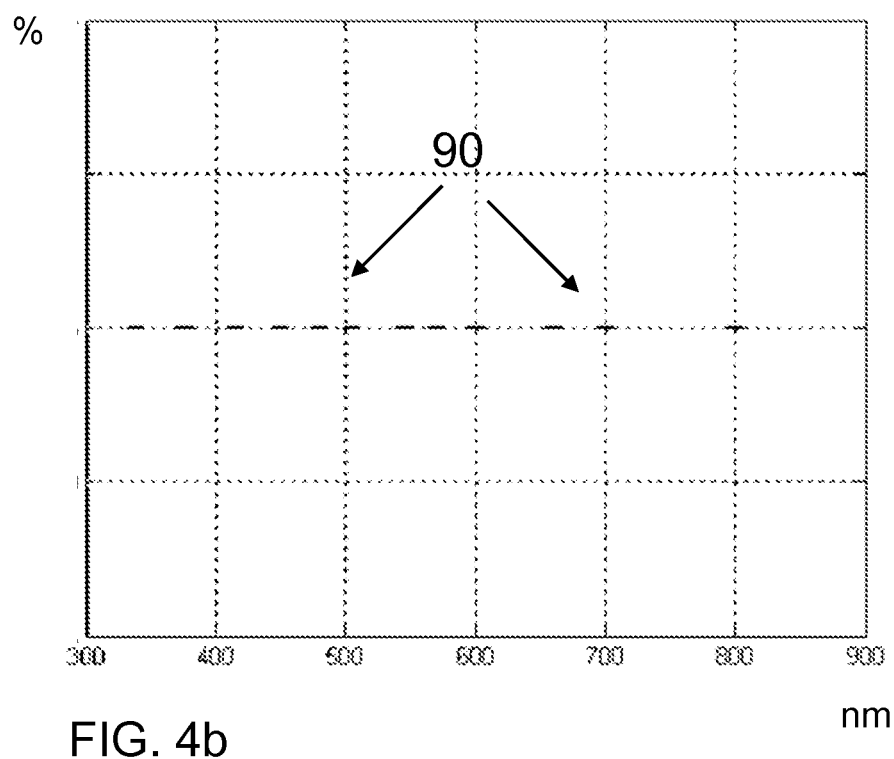
FIG. 4b illustrates the baseline signal at each of the usable wavelength ranges of FIG. 4a according to an embodiment of the present disclosure.

The effect of compensating for the wavelength-dependent responsivity of the detection unit 50 is best understood by comparing FIG. 3a with FIG. 4a and FIG. 3b with FIG. 4b respectively.

The graph of FIG. 3a indicates on the left ordinate axis the intensity values of the light source in milliwatt (mW) at different wavelengths, and in particular at selected usable wavelength ranges (on the abscissa). Discrete light emissions 67 can be obtained with a set of LEDs, each emitting light in a respective usable wavelength range, the resulting intensity spectrum being roughly equivalent to that emitted by a typical halogen broad spectrum lamp used in similar applications. The wavelength-dependent responsivity Rdu ($\lambda$) of a typical state of the art detection unit is indicated by curve Rdu($\lambda$) with reference to the ordinate axis on the right, wherein the unit is Ampere per Watt (A/W).

FIG. 3b depicts the normalized baseline signals 90, indicated in percent (%), obtained at each of the usable wavelength ranges of FIG. 3a according to the formula BL($\lambda$)=S($\lambda$)*Rdu($\lambda$). The term normalized here can mean that the maximum baseline signal can be given a relative value of about 100% and all other baseline signals are expressed as a fraction or % of this relative value. It can be seen that the baseline signal 92 at about 340 nm is only about 0.3% of the baseline signal 91 at about 660 nm (100%) representing the minimum and maximum baseline signal respectively in this range of selected usable wavelengths. The dynamic range of the baseline is in this case about 330:1.

When comparing FIG. 4a with FIG. 3a, the difference is that the intensity of the light emissions 67 of the individual LEDs 61 is adjusted in a manner reciprocal to the wavelength-dependent responsivity Rdu($\lambda$) of the detection unit 50.

FIG. 4b depicts the normalized baseline signals 90, indicated in percent (%), obtained at each of the usable wavelength ranges of FIG. 4a according to the formula BL($\lambda$)=S($\lambda$)*Rdu($\lambda$). In comparison with FIG. 3b, it can be seen that a baseline signal 90 can be obtained, which is the same at each of the selected usable wavelengths. The dynamic range of the baseline can now be reduced to about 1:1.

Figure 4C:
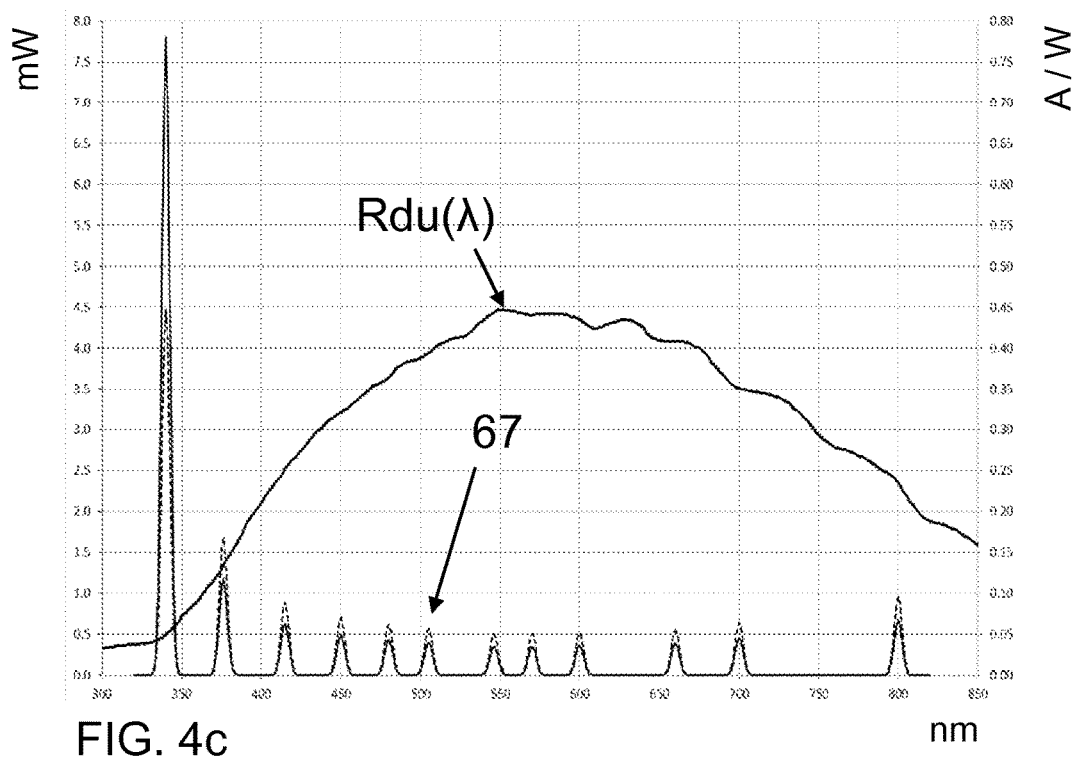
FIG. 4c illustrates in comparison to FIG. 4a, an example of how the light intensity for each of the plurality of light emitting elements is adjusted in order to further reduce stray light effects at one usable wavelength range according to an embodiment of the present disclosure.

FIG. 4c shows the comparison of the same wavelength dependent responsivity of the detection unit Rdu($\lambda$) as well as the same intensity of light emissions 67 (dashed lines) for each of a plurality of light emitting elements emitting light in respective usable wavelength ranges as shown in FIG. 4a.

In addition, on the same graph, FIG. 4c shows with continuous lines one example of how the intensity of the light emissions 67 for each of the plurality of light emitting elements can be adjusted in order to further reduce stray light effects at one usable wavelength range, in this case at about 340 nm. In particular, it can be noted that the intensity of the light emitting element at about 340 nm can be higher than as in FIG. 4a, while all others can be proportionally lower than as in FIG. 4a.

Figure 4D:
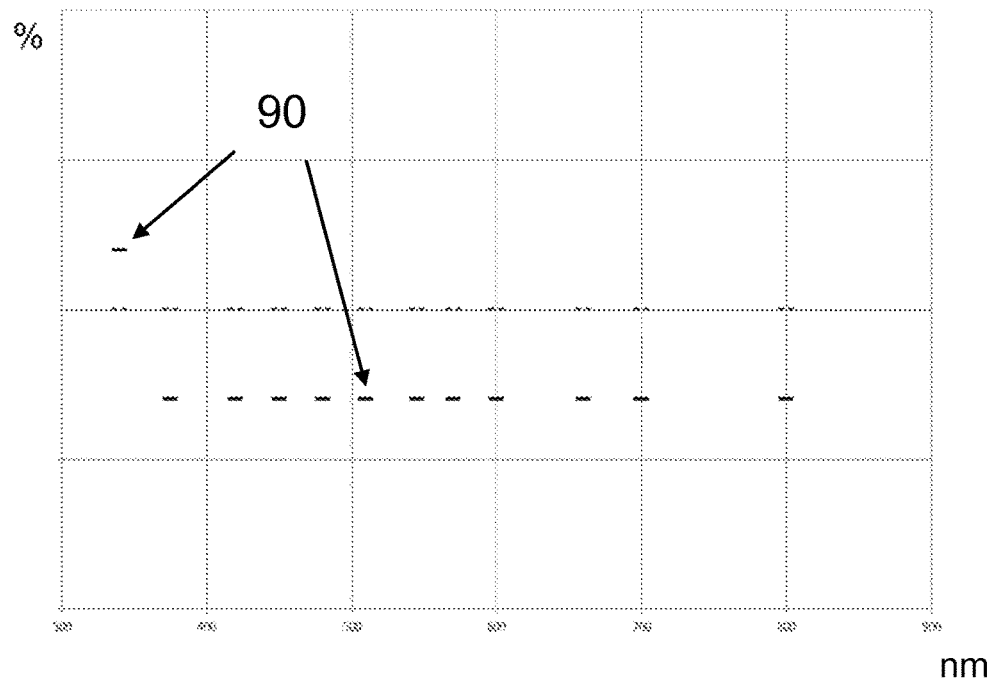
FIG. 4d illustrates how the baseline signals obtained according to the light intensities of FIG. 4c change when compared to those of FIG. 4b according to an embodiment of the present disclosure.

This difference in light intensity can cause a difference in the baseline signals 90 as shown in FIG. 4d when compared to FIG. 4b. The dynamic range of the baseline can be, in this case, still about 1:1 if the first wavelength range at about 340 nm is not taken into account. It can be slightly larger if also the first wavelength range is taken into account, but nevertheless smaller if compared to that of FIG. 3b. This minor increase of dynamic range for one or more usable wavelength ranges may be acceptable when the advantage of reduced stray light is considered.

Figure 5:
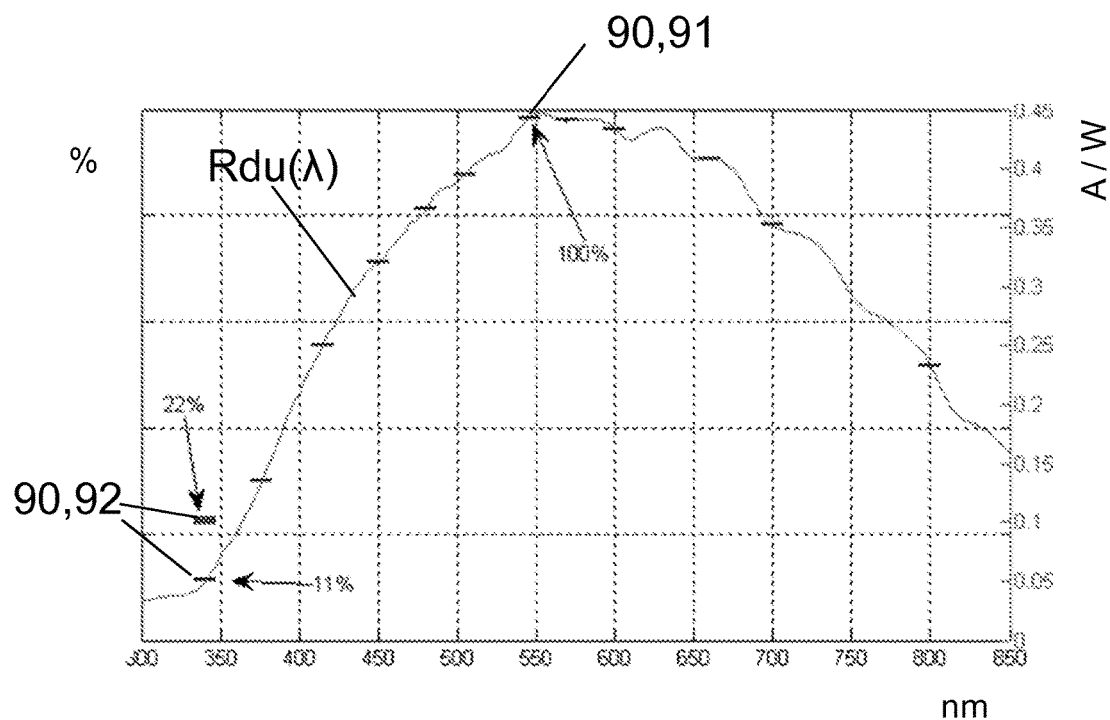
FIG. 5 illustrates how a ratio between the first baseline signal at a first usable wavelength range and the baseline signal at a second usable wavelength range, which is about 50% of the ratio between the responsivity of the detection unit at the first usable wavelength range and the responsivity of the detection unit at the second usable wavelength range is calculated according to an embodiment of the present disclosure.

FIG. 5 depicts the normalized baseline signals 90, indicated in percent (%), obtained at each of the usable wavelength ranges as in FIGS. 3a and 4a according to the formula $BL(\lambda)=S(\lambda)*Rdu(\lambda)$ and assuming that the intensity of the light source was constant at all wavelengths. The baseline signals can thus fit with the responsivity curve of the detection unit $Rdu(\lambda)$. It can be seen that the baseline signal 92 at about 340 nm is only about 11% of the baseline signal 91 at about 550 nm (100%) representing the minimum and maximum baseline signal respectively in this range of selected usable wavelengths. In this case, about 11% can also be the ratio between Rdu at about 550 nm and Rdu at about 340 nm. By increasing the intensity of the light emitting element in the range of about 340 nm so that the minimum baseline signal 92 becomes about 22% of the maximum baseline signal at about 550 nm, the ratio between the maximum baseline signal and the minimum baseline signal can be about 50% of the ratio between the responsivity of the detection unit at about 550 nm and the responsivity of the detection unit at about 340 nm.

Figure 6A:
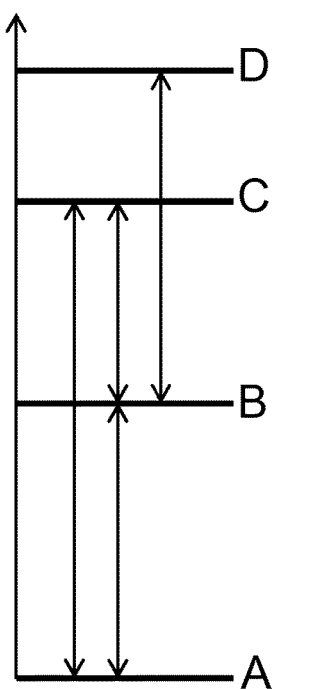
FIG. 6a illustrates schematically the typical state of the art relationship between the dynamic range of the detector, the dynamic range of the baseline and the dynamic range of the analyte concentrations.

FIG. 6a depicts schematically the typical state of the art relationship between the dynamic range AC of the detector (between lines A and C), the dynamic range AB of the baseline (between lines A and B), and the dynamic range BD of the analyte concentrations (between lines B and D). It can be seen that a considerable part of the dynamic range AC of the detector can be used up by the baseline, thus reducing the dynamic range of the detector from AC to BC (between lines B and C). BC can be also defined as the usable dynamic range, or the dynamic range, which can really be available for the measurement of analyte concentrations. If the dynamic range BD of the analyte concentrations exceeds the usable dynamic range BC of the detector, signal saturation may occur and the measurement may need to be repeated after diluting the sample. In the alternative, more complex and expensive detectors with a broader dynamic range may be used.

Figure 6B:
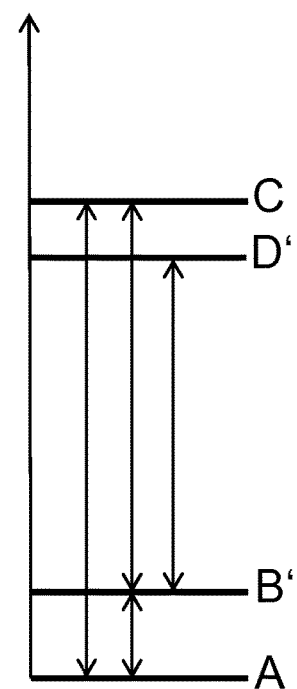
FIG. 6b illustrates schematically the relationship between the dynamic range of the detector, the dynamic range of the baseline and the dynamic range of the analyte concentrations after reducing the dynamic range of the baseline according to an embodiment of the present disclosure.

FIG. 6b depicts schematically the effect of reducing the dynamic range AB' of the baseline signal (between lines A and B'). In particular, it can be seen that the usable dynamic range B'C of the detector (between lines B' and C) can be accordingly increased. The dynamic range B'D' of the analyte concentrations (between lines B' and D') can remain the same as BD in FIG. 6a but the lines can have shifted to be comprised within the dynamic range AC of the detector, which may also remain constant.

According to one embodiment, this can be achieved by providing a light source comprising a plurality of light emitting elements for emitting light of different respective usable wavelength ranges, wherein the intensity of at least some of the light emitting elements can be adjusted to compensate at least in part for the wavelength-dependent responsivity of the detection unit at least with respect to selected usable wavelengths. According to another embodiment, this can be achieved by providing at least one light regulator in the optical path to compensate at least in part for the wavelength-dependent responsivity of the detection unit at least with respect to selected usable wavelengths. According to another embodiment, this can be achieved by sequentially adjusting the intensity of the light source to compensate at least in part for the wavelength-dependent responsivity of the detection unit at least with respect to selected usable wavelengths.

One advantage can be the possibility to make nearly full use of the available dynamic range of the detector for the measurement, that is, for determining the presence and/or concentration of analytes in a sample. Another advantage can be the possibility to use cheaper detectors such as CCD or CMOS detectors. Another advantage can be that while the dynamic range of the detector may be small, the usable dynamic range for detection may be maximized to nearly cover the full available dynamic range of the detector. Another advantage can be that the need to dilute the sample and repeat the analysis if the measured signal was too high can be prevented. Another advantage can be reduction of stray light in the optical device.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A method for increasing dynamic range of detection in optical qualitative and/or quantitative analysis of analytes in a sample with a detection unit having a wavelength-dependent responsivity, the method comprising:

guiding light from a light source comprising at least a first and a second light emitting elements for emitting light of at least a first and a second usable wavelength ranges for a given analyte to the detection unit comprising optical elements in an optical path and a photodetector, wherein the detection unit has a combined wavelength-dependent responsivity ($Rdu(\lambda)$) such that the responsivity of the detection unit is lower at at least the first usable wavelength range and higher at at least the second usable wavelength range, with the light guided through a blank sample or in the absence of the sample such that baseline signals at the usable wavelength ranges are generated, adjusting the intensity of at least the first and the second light emitting elements by varying electrical power input to at least the first and the second light emitting elements so that the intensity of at least the first and the second light emitting elements is inverse to the wavelength-dependent responsivity ($Rdu(\lambda)$) of the detection unit with respect to at least the first and the second usable wavelength ranges respectively, so as to obtain a reduction of the ratio between the maximum and minimum of baseline signals at at least the first and the second usable wavelength ranges, and generating response signals relative to the baseline signals from the sample located in the optical path by the photodetector, wherein the response signals are indicative of the presence and/or concentration of analytes in the sample.

2. The method according to claim 1, wherein the reduction of the ratio between the maximum and minimum of the baseline signals at at least the first and the second usable wavelength ranges is such that the dynamic range of the detector comprises the dynamic range of the analyte concentrations being determined.

3. The method according to claim 2, wherein the reduction of the ratio between the maximum and minimum of baseline signals at at least the first and the second usable wavelength ranges is carried out as a function of the type of the sample or of the type of the analytes being determined.

4. The method according to claim 1, further comprising, compensating at least in part the wavelength-dependent responsivity ($Rdu(\lambda)$) of the detection unit at least with respect to selected usable wavelengths by preamplifiers or electronic filters.

5. The method according to claim 1, wherein the ratio between the maximum and minimum of baseline signals at at least the first and the second usable wavelength ranges is 50% or less of the ratio between the responsivities of the detection unit at at least the first and the second usable wavelength ranges.

6. The method of claim 1, wherein adjusting the intensity of at least the first and the second light emitting elements comprises increasing the intensity of at least the first light source or decreasing intensity of the second light source, or both.

7. The method of claim 1, wherein at least the first and the second light emitting elements are a plurality of light emitting elements and at least the first and the second usable wavelength ranges are a plurality of usable wavelength ranges, and wherein adjusting the intensity of the plurality of light emitting elements occurs sequentially.

8. The method of claim 1, wherein the photodetectors are made of silicon.

* * * * *